United States Patent
Rangaiah

(10) Patent No.: US 8,579,906 B2
(45) Date of Patent: Nov. 12, 2013

(54) APPARATUS AND MEASURING INSTRUMENT

(75) Inventor: Chetan Rangaiah, Rocky Hill, CT (US)

(73) Assignee: Depuy (Ireland) (IE)

( * ) Notice: Subject to any disclaimer, the term of this patent is extended or adjusted under 35 U.S.C. 154(b) by 224 days.

(21) Appl. No.: 13/056,346

(22) PCT Filed: Jul. 27, 2009

(86) PCT No.: PCT/EP2009/059656
§ 371 (c)(1),
(2), (4) Date: Jan. 28, 2011

(87) PCT Pub. No.: WO2010/012679
PCT Pub. Date: Feb. 4, 2010

(65) Prior Publication Data
US 2011/0130766 A1    Jun. 2, 2011

(30) Foreign Application Priority Data

Jul. 29, 2008   (GB) .................................. 0813826.5

(51) Int. Cl.
*A61B 17/60*   (2006.01)
(52) U.S. Cl.
USPC ........................................................ 606/88
(58) Field of Classification Search
USPC .......... 606/86 R–90, 96–98, 102; 269/43, 72, 269/74, 143, 249, 300–301
See application file for complete search history.

(56) References Cited

U.S. PATENT DOCUMENTS

| | | | |
|---|---|---|---|
| 4,843,720 A | | 7/1989 | Kim |
| 5,423,827 A | * | 6/1995 | Mumme et al. ................. 606/96 |
| 5,562,675 A | * | 10/1996 | McNulty et al. ................ 606/96 |
| 5,624,444 A | * | 4/1997 | Wixon et al. ................... 606/88 |
| 5,662,656 A | * | 9/1997 | White ............................. 606/88 |
| 5,810,831 A | * | 9/1998 | D'Antonio ..................... 606/88 |
| 6,290,704 B1 | * | 9/2001 | Burkinshaw et al. .......... 606/88 |
| 6,458,135 B1 | | 10/2002 | Harwin |
| 6,688,012 B1 | * | 2/2004 | Crain et al. .................... 33/296 |

(Continued)

FOREIGN PATENT DOCUMENTS

| EP | 1374784 A1 | 1/2004 |
|---|---|---|
| GB | 660394 A | 11/1951 |

(Continued)

OTHER PUBLICATIONS

PCT International Search Report and Written Opinion PCT/EP2009/059656 dated Jan. 21, 2010.

(Continued)

*Primary Examiner* — Todd Manahan
*Assistant Examiner* — Eric S Gibson

(57) ABSTRACT

An apparatus and measuring instrument includes a first part and a second part slidably moveable with respect to one another. The first part includes a locking member that has a hard portion which is movable from a first position to a second position. The second part includes a compressible portion that has a Shore hardness less than the hard portion and is positioned such that when the locking member is in the first position the compressible portion is not engaged by the hard portion, and when the locking member is in the second position the compressible portion is at least partially compressed by the hard portion thereby preventing relative movement of the first and second parts.

13 Claims, 5 Drawing Sheets

(56) References Cited

U.S. PATENT DOCUMENTS

| | | | |
|---|---|---|---|
| 7,115,133 B2 * | 10/2006 | Plumet et al. | 606/102 |
| 7,175,630 B2 * | 2/2007 | Farling et al. | 606/87 |
| 7,261,719 B1 * | 8/2007 | Twomey et al. | 606/102 |
| 7,451,550 B2 * | 11/2008 | Dees, Jr. | 33/512 |
| 7,682,362 B2 * | 3/2010 | Dees, Jr. | 606/86 R |
| 8,123,758 B2 * | 2/2012 | Metzger et al. | 606/102 |
| 8,216,244 B2 * | 7/2012 | Green et al. | 606/102 |
| 2004/0215205 A1 * | 10/2004 | Plumet et al. | 606/102 |
| 2004/0220583 A1 * | 11/2004 | Pieczynski et al. | 606/102 |
| 2005/0209600 A1 * | 9/2005 | Fencl et al. | 606/89 |
| 2006/0149276 A1 * | 7/2006 | Grimm | 606/88 |
| 2006/0179979 A1 * | 8/2006 | Dees, Jr. | 81/9.2 |
| 2006/0217732 A1 * | 9/2006 | Seo et al. | 606/87 |
| 2007/0149977 A1 * | 6/2007 | Heavener | 606/87 |
| 2007/0173851 A1 * | 7/2007 | McMillen et al. | 606/87 |
| 2009/0143783 A1 * | 6/2009 | Dower | 606/88 |
| 2009/0157157 A1 * | 6/2009 | Schorn et al. | 607/149 |
| 2010/0057090 A1 * | 3/2010 | May et al. | 606/96 |
| 2010/0160919 A1 * | 6/2010 | Axelson et al. | 606/89 |
| 2010/0324563 A1 * | 12/2010 | Green et al. | 606/89 |
| 2011/0046685 A1 * | 2/2011 | Faure et al. | 606/86 R |
| 2011/0130766 A1 * | 6/2011 | Rangaiah | 606/102 |
| 2012/0143205 A1 * | 6/2012 | Dower et al. | 606/102 |

FOREIGN PATENT DOCUMENTS

| | | |
|---|---|---|
| GB | 2167999 A | 6/1986 |
| WO | WO 0013594 A1 | 3/2000 |
| WO | WO 2007007067 A2 | 1/2007 |

OTHER PUBLICATIONS

UKIPO Search Report GB0813826.5 dated Oct. 27, 2008.

* cited by examiner

APPARATUS AND MEASURING INSTRUMENT

CROSS REFERENCE TO RELATED APPLICATION

This application is a National Stage 35 U.S.C. 371 of International Patent Application PCT/EP2009/059656 filed Jul. 27, 2009.

BACKGROUND OF THE INVENTION

The present invention relates to an apparatus for locking relative sliding movement of first and second parts. In particular the present invention relates to a measuring instrument for use in surgery including such an apparatus.

In orthopaedic surgery, for example knee replacement surgery, parts of a joint which are damaged are replaced with a prosthesis. In knee replacement surgery one such prosthesis is a femoral prosthesis which is affixed to the femur to provide a replacement bearing surface for the knee joint. Before fitting the prosthesis it is necessary to prepare the femur for the implant by cutting a receiving surface on the bone and locating the correct position for positioning pins. The femoral prosthesis is available in a number of different sizes to suit the anatomy of the patient. A measuring instrument is used to determine the size of the implant and to ensure that any holes for receiving positioning pins of a prosthesis are in the correct position.

A typical known femoral sizing guide is an instrument made entirely of metal or metal alloy. It comprises parts that can slide relative to one another to measure the anatomy of the patient and determine the correct size of implant. Once the correct size has been determined, it is desirable to lock the parts, so that they cannot move relative to each other. This is achieved using a knob-based friction lock. A threaded bore is provided in one part above a surface on the other part. A threaded knob is then screwed into the bore so that one end protrudes out of the bore and further rotation of the threaded knob into the bore causes it contact and press on the other part, locking the two parts against relative movement by friction. As the instrument is made of metal there is no significant compression or deformation when the threaded knob is used to lock the parts against relative movement This friction based locking using threaded knobs can be cumbersome to use with gloved hands in a fluid filled wound in the operating room. However, with alternative constructions it can difficult to provide sufficient friction to lock the two parts against relative movement without the mechanical advantage of the threaded knob.

BRIEF SUMMARY OF THE INVENTION

The present invention provides an apparatus which allows relative sliding movement between two parts to be locked selectively. The apparatus comprises a hard part and a softer, or compressible part. In the locked position the harder part acts on the compressible part to lock the two parts against relative movement. The differing material properties of the harder part and the compressible part allow the locking to be achieved more easily and enable the apparatus to be locked without requiring a threaded bore and corresponding threaded knob.

According to a first aspect of the present invention there is provided an apparatus comprising:
a first part and a second part configured for sliding movement relative to each other; and wherein
the first part comprises a locking member comprising a hard portion movable from a first position to a second position; and
the second part comprises a compressible portion which has a Shore hardness less than the hard portion and is positioned such that when the locking member is in the first position the compressible portion is not engaged by the hard portion, and when the locking member is in the second position the compressible portion is at least partially compressed by the hard portion thereby preventing relative movement of the first and second parts.

According to another aspect of the invention, there is provided an apparatus comprising:
a first part and a second part configured for sliding movement relative to each other; and wherein
the first part comprises a locking member comprising a compressible portion movable from a first position to a second position; and
the second part comprises a hard portion which has a Shore hardness greater than the compressible position and is positioned such that when the locking member is in the first position the compressible portion is not engaged by the hard portion, and when the locking member is in the second position the compressible portion is at least partially compressed by the hard portion thereby preventing relative movement of the first and second parts. (The apparatus of this aspect is very similar to the first aspect except that in this aspect the compressible material is provided on the locking member and not the second part).

The interaction between the compressible portion and hard portion controls whether the first and second parts are locked against relative movement. In the second position the hard portion is in contact with and applying a force to the compressible portion. As the compressible portion has a Shore hardness less than the hard portion, the compressible portion, compresses or deforms around the hard portion. This compression creates friction to lock the first and second parts with a fine level of adjustment which would not be possible with a system based on indentations or on a ratchet (where the level of adjustment is limited to the specific indentations provided). Although a similar fine adjustment could be obtained with a prior art threaded knob system, the present invention uses differing materials, one of which has a Shore hardness less than the other, allowing secure locking without the difficult to use threaded knob of the prior art.

The compressible portion may comprise a material with a Shore hardness from about 50 to about 70, more preferably from 58 to 62. One example of a suitable material for the compressible portion is 60 Shore hardness Silicone Rubber.

The hard portion may comprise a material with a Shore hardness of 80 or more. Examples of suitable materials are Pantone 1T cool grey (white) SG85 Polyurethane casting resin, aluminium and stainless steel.

In one embodiment, the hard portion is an edge. The edge may be sharp or rounded and serves to concentrate the force exerted on the compressible portion in the second position, so that the compressible portion is further compressed, further securing the two parts together in the second position.

In one embodiment, the first part has a longitudinal axis and the first and the second part are configured for sliding movement relative to each other substantially in the direction of the longitudinal axis. The hard portion is straight and aligned substantially perpendicular to the longitudinal axis and the locking member is movable in a direction parallel to the sharp edge between first and second positions. This configuration provides enhanced locking because the hard portion is oriented so that the compressible material is compressed perpendicular to the direction of relative movement. Any resilient reaction force exerted by the compressible portion on the hard portion is perpendicular to the direction in which the locking member is moved between the first and second positions, so any force trying to move the locking member out of the second position is minimised, giving a more secure lock. Another advantage is that in the second position the compressible material is likely to deform locally around the hard portion further improving the security of the second, locked position. In some embodiments, the hard portion may be straight and sharp, so the compressible portion is partly cut into but the hard portion, further securing the lock.

The compressible portion may comprise an infrangible material. A material which is infrangible resists breakage into other pieces. This is desirable in a medical application because it reduces the risk of debris from the compressible portion being broken off by the hard part and falling into the wound.

In order to further minimise any risk from debris, the compressible portion may be made from a biocompatible material.

The compressible portion may be resilient, so that after compression it returns to its original shape. If the compressible portion is resilient the apparatus can be reused more easily because once the locking member has been moved out of the second position, the resilience of the compressible portion will return it to its uncompressed shape, rather than leaving permanent deformation.

The apparatus can form part of a measuring instrument for use in surgery. The measuring instrument may be disposable. In one embodiment, the measuring instrument may be for sizing a femur in knee surgery, and further comprise a stylus attached to the first part or second part. The measuring instrument may also further comprise a positioning guide attached to the first or second part.

BRIEF DESCRIPTION OF THE DRAWINGS

Embodiments of the invention will now be described by way of example with reference to the accompanying drawings, in which like reference numerals refer to like parts and in which.

DETAILED DESCRIPTION OF THE INVENTION

Figure 1:
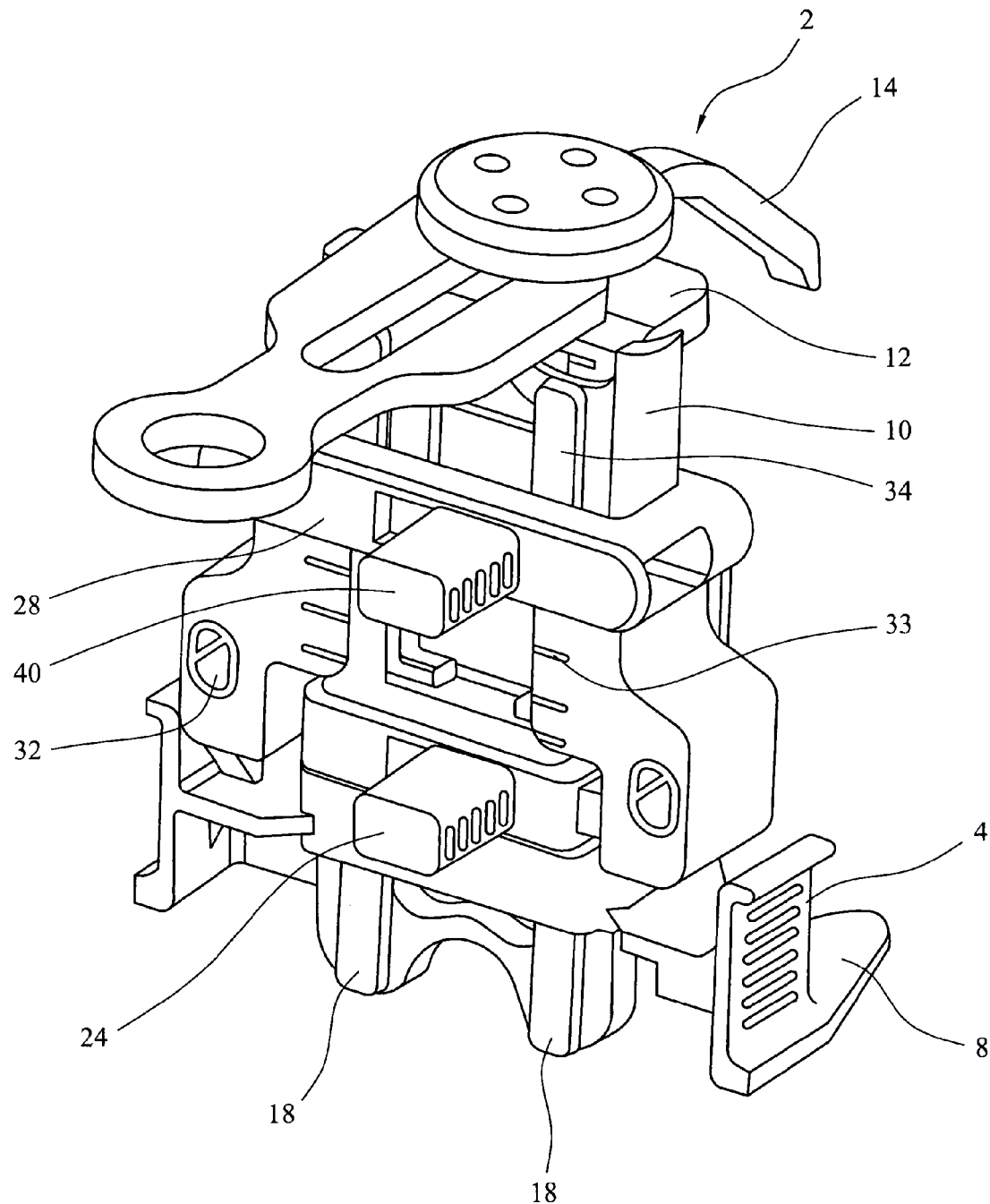
FIG. 1 is a perspective view of an embodiment according to the present invention.

FIG. 1 depicts a perspective view of a measuring instrument 2 for use in knee surgery according to the present invention. It can be used to size a femur and ensure correct positioning in the femur of the positioning pins of a femoral prosthesis. The instrument 2 comprises a main frame 4 which forms one part of two sliding sub-assemblies 6, 9 which are depicted in isolation from each other in FIGS. 2 to 5.

The main frame 4 has a pair of flat feet 8 on it's bottom edge which are placed on a resected tibial surface in use. The main frame 4 extends upwards from the feet 8 generally along a longitudinal axis which is perpendicular to the plane of the feet 8. A channel 10 is defined for receiving the first sliding sub-assembly 6. The external surface around the channel 10 has a generally constant cross section perpendicular to the longitudinal axis to allow the second sliding sub-assembly 9 to partially surround the channel. In this way both of the sliding sub-assemblies 6, 9 can slide relative to the channel 10 in the direction of the longitudinal axis.

Figure 2:
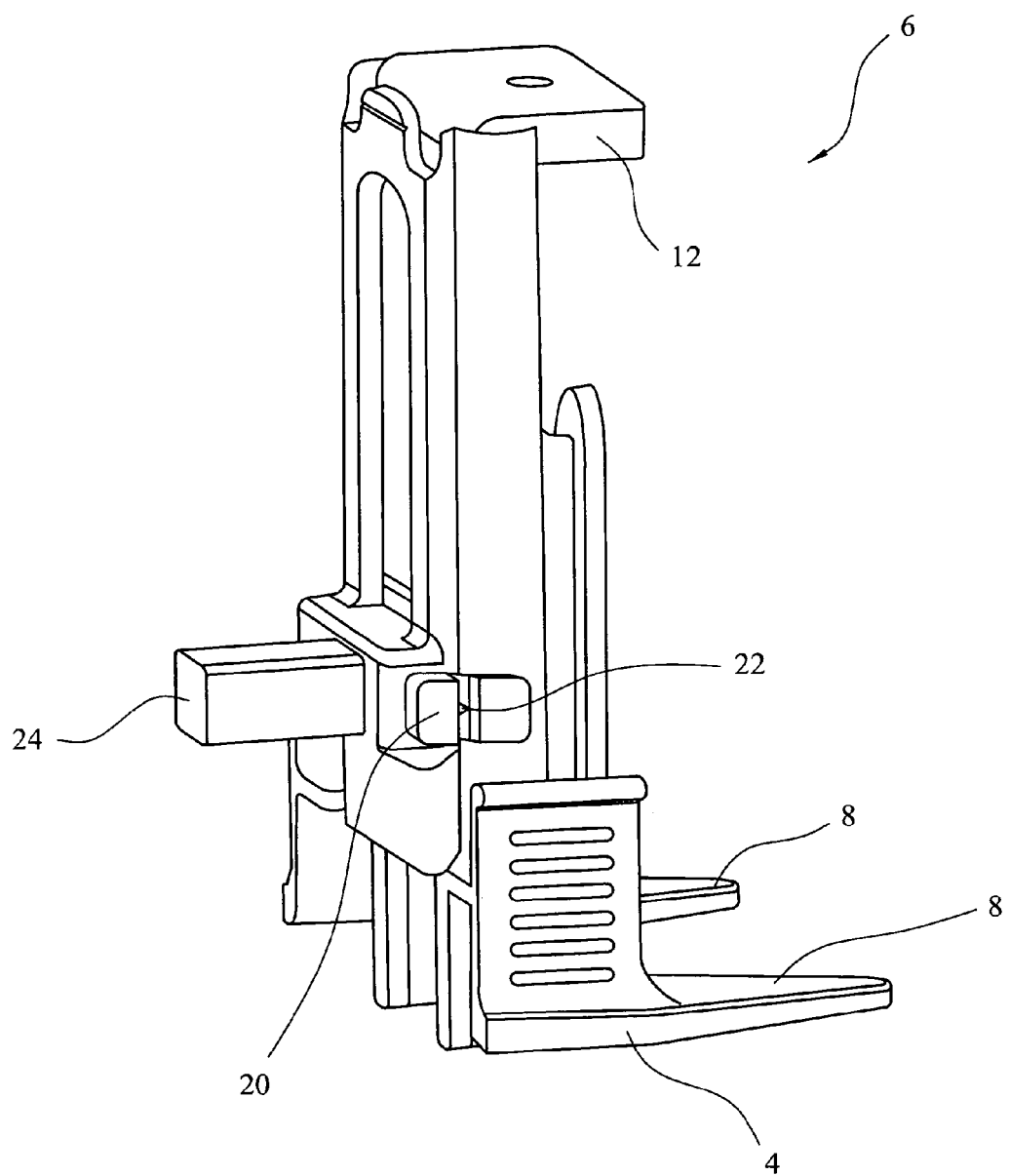
FIG. 2 is a perspective view of a first sub-assembly of the embodiment of FIG. 1.
Figure 3:
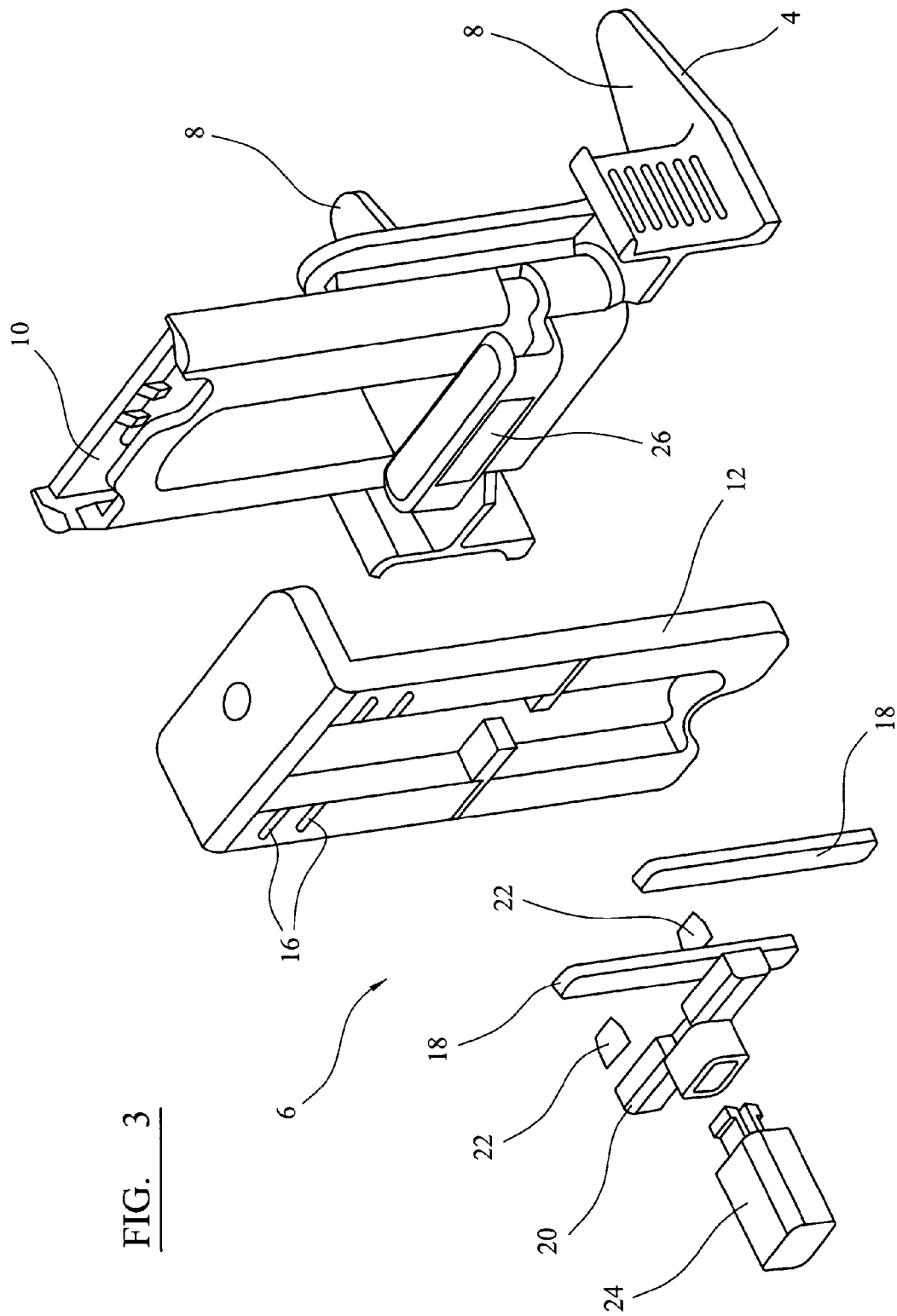
FIG. 3 is an exploded view of the sub-assembly of FIG. 2.

Referring now to FIGS. 2 and 3, the main frame 4 is depicted with the first sliding sub-assembly 6 assembled in FIG. 2 and exploded in FIG. 3 (All the parts relating only to the second sliding sub assembly 9 are omitted for clarity). The first sliding sub-assembly 4 comprises a base plate 12 which is sized to fit within the channel 10 of the main frame 4. The top of the base plate 12 is for connection of a stylus 14 (not shown in FIGS. 2 and 3, but shown in FIG. 1). The base plate 12 has gradation markings corresponding to the sizes of implant used in the knee replacement system, for example the sizes of 2, 2.5, 3, 4, and 5 used in the P. C. S. Sigma Total Knee system commercially available from DePuy International Limited.

Two compressible strips 18 are attached to each side of the base plate 12 and together with the base plate define a perimeter about the longitudinal axis which is slightly smaller than the cross section of the channel 10, allowing the base plate 12 to slide in the channel.

A first locking member 20 is housed within the main frame 4 in the assembled instrument. Hard blades 22 are attached to one end of the first locking member 20 and a grip 24 attached to the other end. The grip 24 protrudes out of an aperture 26 formed in the main frame 4 to allow the first locking member to be moved from a first position to a second position in a direction perpendicular to the longitudinal axis.

In the first position, the hard blades 22 are positioned to the side of the compressible strips 18, allowing the base plate 12 to slide freely in the channel 10. In the second position the hard blades 22 engage the compressible strips 18, compressing them. The blades are oriented parallel to the direction in which the locking member 20 moves, so that it is easier to move the locking member between the first and second positions. In the second position the compression of the compressible strips 18 creates a friction force which locks the base plate 12 relative to the main frame 4.

Figure 4:
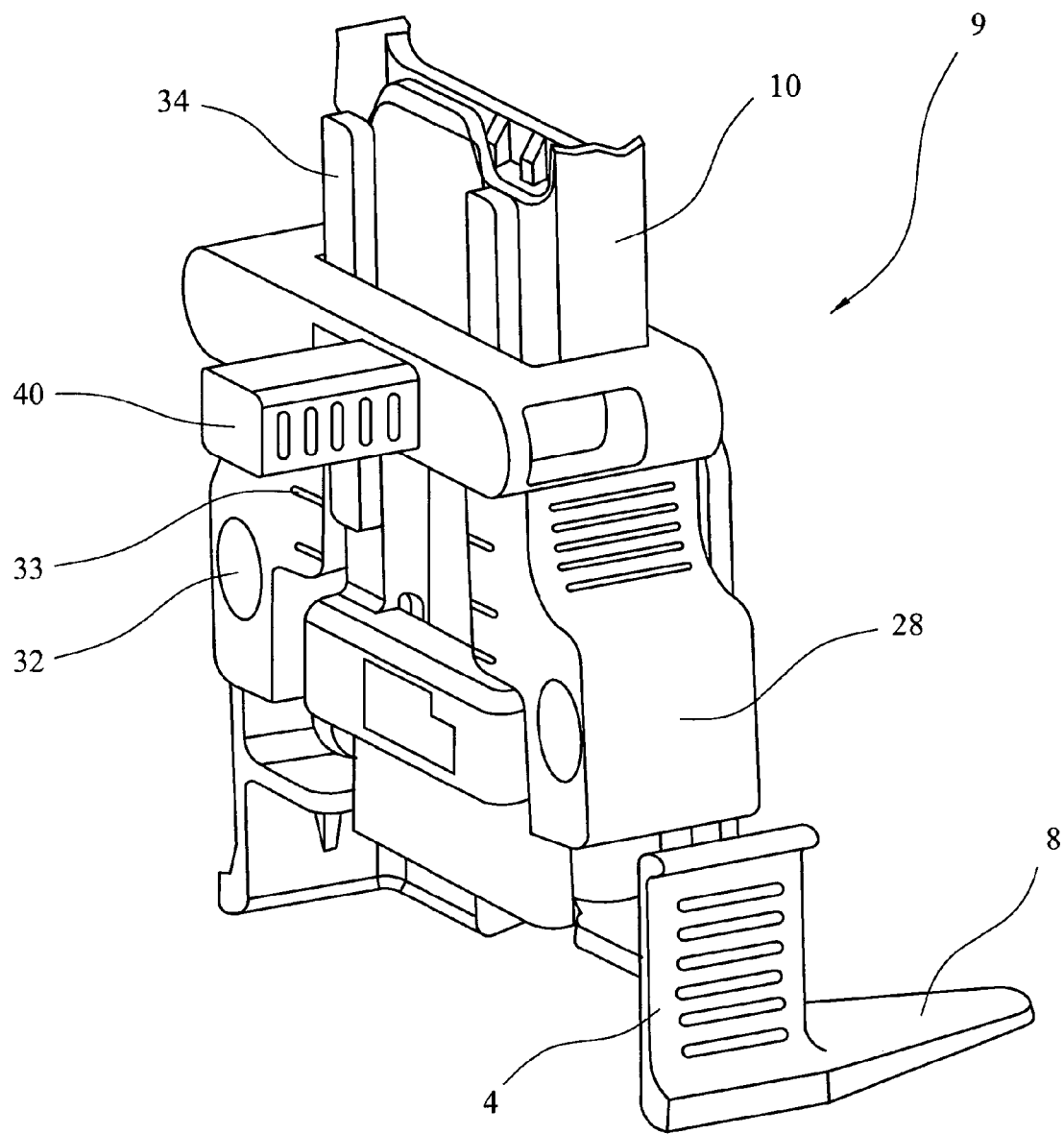
FIG. 4 is a perspective view of a second sub-assembly of the embodiment of FIG. 1.
Figure 5:
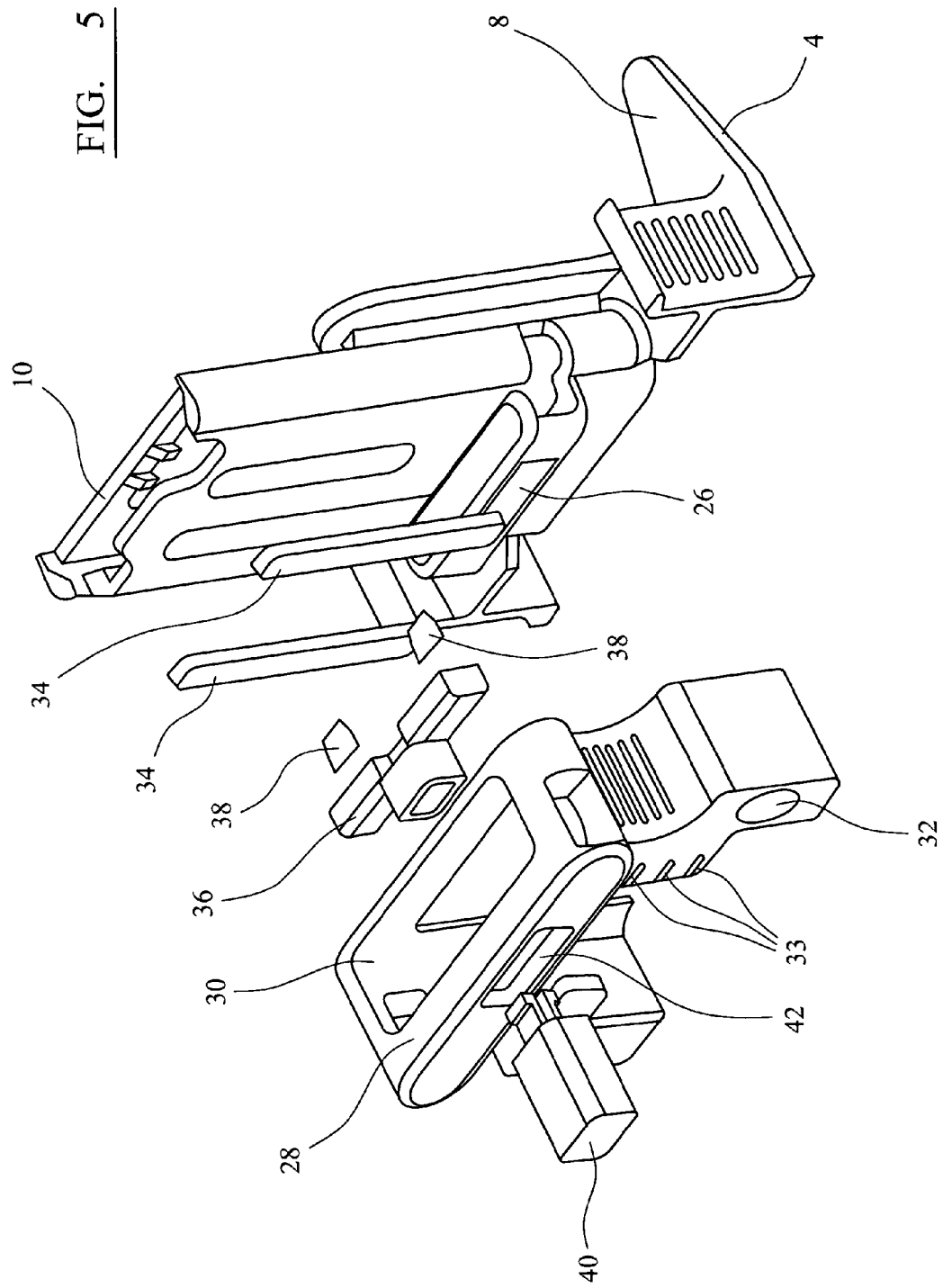
FIG. 5 is an exploded view of the sub-assembly of FIG. 4.

Referring now to FIGS. 4 and 5, the main frame 4 is depicted with the second sub-assembly 9 assembled in FIG. 4 and exploded in FIG. 5. In FIGS. 4 and 5 any components relating only to the first sub-assembly 6 have been omitted for clarity. The second sub-assembly 9 comprises a sliding frame 28 which defines a channel 30 sized so that the external surface of the channel 10 of the main frame 4 fits within the channel 30, enabling the sliding frame 28 to slide in the direction of the longitudinal axis relative to the main frame 4. The sliding frame 28 also defines two apertures 32 for indicating where the positioning pins should be located. Gradation marks 33 are provided on the surface of the sliding frame and mark the same sizes as the base plate 12, i.e. standard sizes of 2, 2.5, 3, 4 and 5 in this embodiment.

The apertures 32 for indicating the placement of positioning pins also function as guides to create the holes for the pins. These apertures 32 are lined with 17-4 Stainless Steel.

Two compressible strips 34 are attached to the external surface of the channel 10 of the main frame 4. A second locking member 36 is provided in the sliding frame 28. Two hard blades 38 are attached to one end of the second locking member 36 and a grip 40 extends from the other end. The sliding frame 28 includes an aperture 42 through which the grip extends when the apparatus is assembled. The second locking member can be moved from side-to-side within the sliding frame 28 between a first position and second position.

In the first position the hard blades 38 are not in contact with the compressible strips 34 and the sliding frame 28 can be slid relative to the main frame 4. In the second position the hard blades 38 engage the compressible strips 34, compressing them. The blades are oriented parallel to the direction in which the locking member 36 moves, so that it is easier to move the locking member between the first and second positions. In the second position the compression of the compressible strips 34 creates a friction force which locks the sliding frame 28 relative to the main frame 4.

In this embodiment the compressible strips 18, 34 are made from 60 Shore hardness Silicone Rubber with a pot life of 60 minutes, a die molding time of 12-14 hours, a viscosity of 3.5 Ms/m$^2$, a Shore hardness of 60±2, a tearing strength of 4 N/mm$^2$, and a tensile strength of 3±0.5 N/mm$^2$. The hard blades 22, 38 are made from 17-4 Stainless steel. This combination of materials provides a good lock when the locking members 20, 36 are moved into the second, locked position. The 60 Shore hardness silicone Rubber compresses and deforms under the blade while resisting cutting and shearing under the force applied by the blade so that it performs as a substantially infrangible material which is resistant to breakage under the blade. Even in the event that debris from compressible strip does break away and fall into a wound in use, 60 Shore hardness silicone Rubber is biocompatible.

The base plate 12 and the stylus 14 are made from Aluminium.

The remaining parts of the apparatus are manufactured from hard plastic. One presently preferred material is Pantone 1T cool grey (white) SG 95 Polyurethane casting resin with a specific gravity of 1.6 (kg/dm$^3$), pot life (200 gm at 20 C) of 5 minutes, a curing time of 45 minutes, a Shore Hardness of 80, a compressive strength of 47 N/mm$^2$, a tensile strength of 27 N/mm$^2$ and a flexural strength of 40 N/mm$^2$.

In use the measuring instrument 2 is placed on a resected tibia so that the feet 8 rest on the resected surface with the femur rotated to 90 degrees. The base plate 12 is then adjusted until the stylus contacts the patent and locked using locking member 20. The gradations 16 can then be read for the size of implant required. This measures the required size of a femoral implant, measuring from the posterior condyles to the anterior notch.

The sliding frame 28 is then adjusted relative to the main frame 4 until the correct prosthesis size, as previously measured, is indicated by the gradations 33. The sliding frame 28 is locked in position using the second locking member 36 so that the apertures 32 can be used to guide the location of the positioning pins.

The femoral implant is usually sized up to the next largest size. For example, if the size is measured between size four and size five, size five is selected and the sliding frame 28 is locked at the size five position.

The measuring instrument may be re-usable or only be used a specific number of times. The extent to which the instrument is re-usable will be determined by the wear on the compressible strips 18, 34. If the compressible strips 18,34 become worn or cut after the blades 38 have engaged them, it will not be possible to reuse the device. However, the use of low-cost materials enables the measuring instrument to be designed for disposal after use in surgery, reducing the requirement for sterilisation.

Although the above-described embodiment uses hard blades with a straight edge to act on the compressible strips, the benefit of selective locking can be achieved with numerous other configurations. For example a hard surface may be used rather than a hard edge.

In an alternate embodiment the placement of the hard surface and the compressible strips may be swapped, so that the compressible strips are located on the locking member and the hard surface on the other part.

In alternate embodiments other numbers of compressible strips than two may be used, for example a single strip or three or more.

It will be appreciated that the mechanism of locking sliding movement by the interaction of a blade and compressible strip can be applied in any situation where selective locking of sliding parts is required, it is not limited to the specific measuring apparatus described above.

Although the above described embodiment has been described with reference to preferred materials, other materials may also be used providing the compressible strips have a lower Shore Hardness than the hard blades.

The invention claimed is:

1. An apparatus for use in surgery, comprising:
    a frame and a plate; the frame and the plate being slidable with respect to one another along a longitudinal axis; wherein one of the frame and the plate has a first aperture that extends along an aperture axis, the aperture axis being substantially perpendicular to the longitudinal axis; and wherein the plate comprises a compressible portion having a first Shore hardness that extends along the longitudinal axis; and
    a locking member at least partially disposed within the first aperture, the locking member comprising a hard portion, the hard portion having a second Shore hardness that is greater than the first Shore hardness, the locking member being slidable along the aperture axis from a first position within the first aperture, whereat the locking member does not engage the compressible portion, to a second position within the first aperture, whereat the locking member at least partially compresses the compressible portion.

2. The apparatus of claim 1, wherein the first Shore hardness ranges from 50 to 70.

3. The apparatus of claim 1, wherein the second Shore hardness is at least 80.

4. The apparatus of claim 1, wherein the hard portion is an edge of the locking member.

5. The apparatus of claim 1, wherein the compressible portion comprises an infrangible material.

6. The apparatus of claim 1, wherein the compressible portion is resilient.

7. The apparatus of claim 1, wherein the apparatus is disposable.

8. The apparatus of claim 1, further comprising a stylus attached to one of the frame and plate.

9. The apparatus of claim 1, further comprising a positioning guide attached to one of the frame and plate.

10. The apparatus of claim 1, wherein the compressible portion is configured to be in the form of a strip.

11. The apparatus of claim 1, wherein the frame has a second aperture configured to receive at least a portion of the plate, and wherein at least a portion of the frame is disposed about the plate and is slidable thereon along the longitudinal axis.

12. The apparatus of claim 1, wherein the frame has a channel and at least a portion of the plate is configured to slide within the channel.

13. The apparatus of claim 1, wherein the plate has a second aperture extending along the longitudinal axis, the second aperture sized to accept at least a portion of the locking member.

* * * * *